(12) United States Patent
Liu et al.

(10) Patent No.: US 7,247,693 B2
(45) Date of Patent: Jul. 24, 2007

(54) MONOMER COMPOUND COMPRISING SEVERAL CATIONIC GROUPS, PROCESS FOR MAKING THE SAME, AND POLYMERS COMPRISING UNITS DERIVING THEREFROM

(75) Inventors: Leo Zhaoqing Liu, Lawrenceville, NJ (US); Dominic Wai-Kwing Yeung, Mississauga (CA)

(73) Assignee: Rhodia Inc., Cranbury, NJ (US)

( * ) Notice: Subject to any disclaimer, the term of this patent is extended or adjusted under 35 U.S.C. 154(b) by 0 days.

(21) Appl. No.: 11/327,014

(22) Filed: Jan. 6, 2006

(65) Prior Publication Data
US 2006/0111533 A1 May 25, 2006

Related U.S. Application Data

(62) Division of application No. 10/453,240, filed on Jun. 3, 2003, now Pat. No. 7,030,275.

(60) Provisional application No. 60/385,714, filed on Jun. 4, 2002.

(51) Int. Cl.
*C08F 20/56* (2006.01)
*C08F 20/60* (2006.01)

(52) U.S. Cl. ...... 526/307; 526/287; 526/288; 526/304; 526/306; 526/312; 526/317.1; 526/318.2; 526/319; 526/320; 526/330; 526/332; 526/342; 526/347

(58) Field of Classification Search ...... 526/304, 526/306, 307, 312, 319, 332, 287, 288, 317.1, 526/318.2, 320, 330, 342, 347; 564/281, 564/292; 560/128
See application file for complete search history.

(56) References Cited

U.S. PATENT DOCUMENTS

| | | | |
|---|---|---|---|
| 4,180,643 A | 12/1979 | Moss et al. | 528/52 |
| 4,212,820 A | 7/1980 | Hotchkiss et al. | 260/561 |
| 4,387,017 A | 6/1983 | McEntire et al. | 208/188 |
| 4,536,305 A | 8/1985 | Borchardt et al. | 252/8.55 R |
| 6,077,461 A | 6/2000 | Murray et al. | 252/700 |
| 6,569,261 B1 | 5/2003 | Aubay et al. | 134/39 |

FOREIGN PATENT DOCUMENTS

| | | |
|---|---|---|
| EP | 156 747 | 7/1988 |
| JP | 4-187663 | 7/1992 |

OTHER PUBLICATIONS

D. Joynes & D.C. Sherrington, "Novel Polymerizable Mono—and Divalent Quaternary Ammonium Cationic Surfactants: I. Synthesis, Structural Characterization and Homopolymerization," POLYMER vol. 37, No. 8, 1996, pp. 1453-1462.

*Primary Examiner*—Helen L Pezzuto

(57) ABSTRACT

A polymer includes repetitive units derived from a monomer compound according to formula (I):

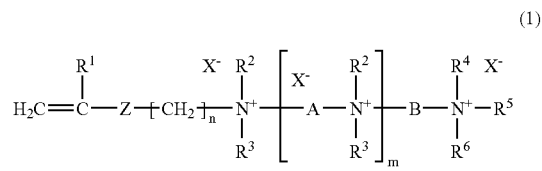

wherein $R^1$ is a hydrogen atom, a methyl group or an ethyl group, A, which is identical or different, is a group comprising an ester group of formula $-A^1-C(O)-O-A^2-$, or an amide group of formula $-A^1-C(O)-NR^{10}-A^2-$, wherein: $R^{10}$, which is identical or different, is hydrogen or an alkyl, hydroxyalkyl, or aminoalkyl $C_1-C_6$ linear or branched group, $A^1$, which is identical or different is a covalent bond or a group of formula $-(CH_2)_{p1}-$ wherein p1 is an integer of from 1 to 6, $A^2$, which is identical or different, is a linear or branched hydrocarbon group comprising optionally N, O, or S heteroatoms or heterogroups, optionally substituted, optionally forming or comprising a cycle, $R^1, R^2, R^3, R^5$ and $R^6$, which are identical or different, are hydrogen, alkyl, hydroxyalkyl, or aminoalkyl $C_1-C_6$ linear or branched groups, or, if inside the brackets, form a heterocycle with group $A^2$, m is an integer of from 1 to 10, n is an integer of from 1 to 6, Z is $-O-$, $-C(O)O-$, or $-C(O)NH-$, B is a linear or branched $C_2-C_{12}$ polymethylene chain, optionally comprising heteroatoms or heterogroups, and optionally substituted with one or several hydroxy or amino groups, and $X^-$, which are identical or different, are counter ions.

8 Claims, No Drawings

MONOMER COMPOUND COMPRISING SEVERAL CATIONIC GROUPS, PROCESS FOR MAKING THE SAME, AND POLYMERS COMPRISING UNITS DERIVING THEREFROM

This application is a divisional of 10/453,240, filed on Jun. 3, 2003, now U.S. Pat. No. 7,030,275, which claims benefit of 60/385,714, filed Jun. 4, 2002.

BACKGROUND OF THE INVENTION

The invention relates to monomer compounds comprising several cationic groups. The invention also relates to a process for making these monomer compounds. The process is highly selective and prevents unwanted reactions leading to undesired structures. The invention relates also to polymers, including copolymers, comprising units deriving from said monomer compounds.

Polymers, and especially copolymers, comprising cationic units are useful in various applications. In formulations, for example in home care formulations, personal care formulations, or formulations used in oil-field industry, the cationic units may interact with other compounds, such as surfaces, surfactants or active ingredients, and provide specific properties. Various polymers and copolymers comprising cationic units are used. Some properties and/or structures of formulation can be tuned by using copolymers comprising several cationic units. Developing new monomers and therefore new polymers or copolymers allow developing new formulations with either environment protection improvements, or of course new properties or functions.

Copolymers comprising units that comprise two cationic groups (hereafter referred to as di-cationic units), and preparation thereof, have been described, and are used for example in personal care formulations such as shampoos, and in hard surface cleaning formulations. There is a need for polymers and copolymers comprising units that comprise at several cationic groups (hereafter referred to as poly-cationic units, for example di-cationic units, tri-cationic units or tetra-cationic units). Hence, there is a need for monomers comprising several cationic groups (hereafter referred to as poly-cationic monomers, for example di-cationic, tri-cationic monomers or tetra-cationic monomers), and for efficient processes for preparing them.

Poly-cationic monomers, and copolymers comprising poly-cationic units are described in published patent application WO 01/05920. This documents describes for example poly-cationic monomers having the following formula:

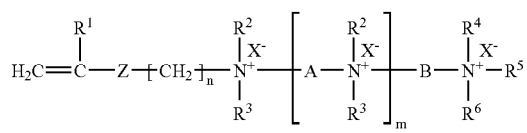

wherein
$R_1$ is a hydrogen atom or a methyl or ethyl group;
$R_2$, $R_3$, $R_4$, $R_5$ and $R_6$, which are identical or different, are linear or branched $C_1$-$C_6$, preferably $C_1$-$C_4$, alkyl, hydroxyalkyl or aminoalkyl groups;

m is an integer from 1 to 10, for example 1;
n is an integer from 1 to 6, preferably 2 to 4;
Z represents a —C(O)O— or —C(O)NH— group or an oxygen atom;
A represents a $(CH_2)_p$ group, p being an integer from 1 to 6, preferably from 2 to 4;
B represents a linear or branched $C_2$-$C_{12}$, advantageously $C_3$-$C_6$, polymethylene chain optionally interrupted by one or more heteroatoms or heterogroups, in particular O or NH, and optionally substituted by one or more hydroxyl or amino groups, preferably hydroxyl groups;
X, which are identical or different, represent counterions;

The poly-cationic monomers describes in this document are prepared by a process according to the following schemes:

-Reaction scheme No. 1:

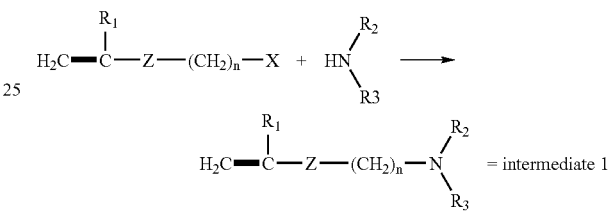

-Reaction scheme No. 2:
(when m is equal to 1)

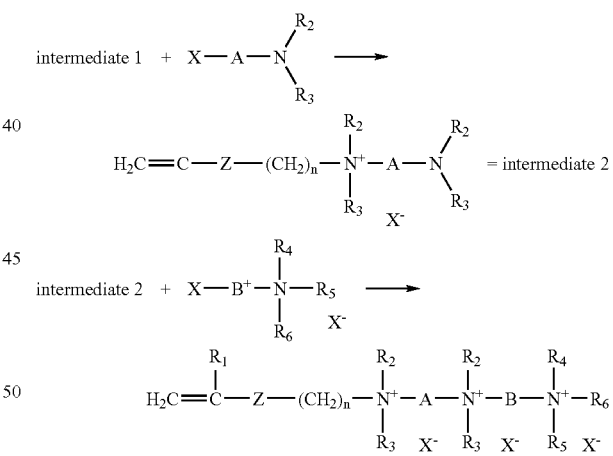

-Reaction scheme No. 3:
(when m is between 2 and 10)

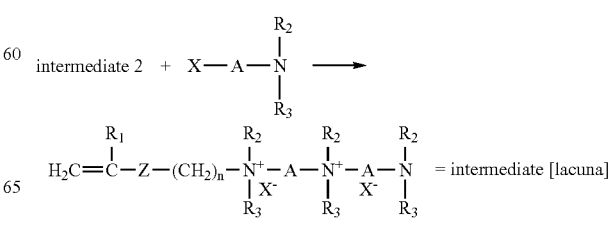

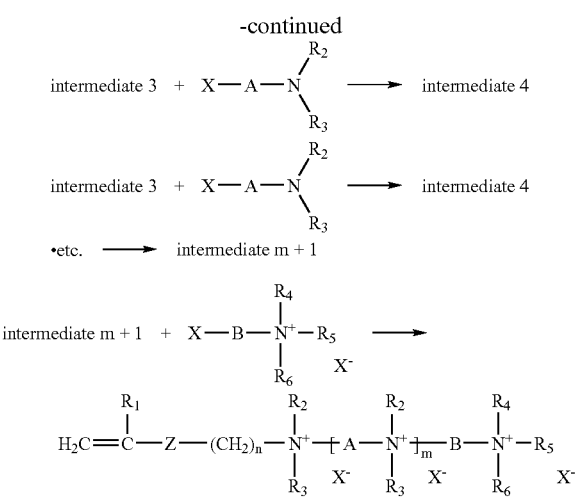

The reaction schemes described in that document are not highly selective. Presence of undesired products may alter polymers or copolymers properties and therefore alter properties in a formulation comprising said polymers or copolymers. Purification steps of product obtained by this reaction scheme may be either expensive or difficult.

The invention provides a new process which is more efficient (as purity, selectivity, and yield balance). It provides new poly-cationic monomers that are particularly useful in designing polymers or copolymers, and tuning properties and/or structures of formulations comprising said polymers or copolymers. It allows for example tuning interactions of said polymers or copolymers with other compounds comprised in the formulation such as surfactants, other polymers, and actives, or interactions with an application field of the formulation, such as surfaces, and compounds comprised in the formulation applications field). Such copolymers are particularly useful in home-care formulations (e.g. detergent formulations, hard surface cleaning formulations) or personal-care formulations (e.g. shampoos)

BRIEF SUMMARY OF THE INVENTION

A first aspect, the invention relates to a monomer compound comprising several cationic groups having the following formula (I):

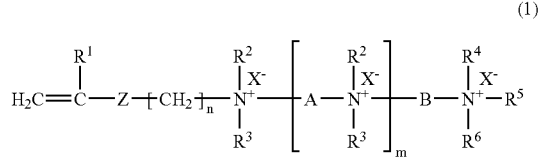

wherein
$R^1$ is a hydrogen atom, a methyl group or an ethyl group,
A, which is identical or different, is a group comprising an ester group of formula
-$A^1$-C(O)—O-$A^2$-, or an amide group of formula -$A^1$-C(O)—$NR^{10}$-$A^2$-, wherein:

$R^{10}$, which is identical or different, is hydrogen or an alkyl, hydroxyalkyl, or aminoalkyl $C_1$-$C_6$ linear or branched group, $A^1$, which is identical or different is a covalent bond or a group of formula —$(CH_2)_{p1}$— wherein p1 is an integer of from 1 to 6, preferably 1, $A^2$, which is identical or different, is a linear or branched hydrocarbon group comprising optionally N, O, or S heteroatoms or heterogroups, optionally substituted, optionally forming or comprising a cycle, such as a heterocycle, $A^2$ preferably being a group of formula —$(CH_2)_{p2}$— wherein p2 is an integer of from 1 to 6, $R^1$, $R^2$, $R^3$, $R^5$ and $R^6$, which are identical or different, are hydrogen, alkyl, hydroxyalkyl, or aminoalkyl $C_1$-$C_6$ linear or branched groups, or, if inside the brackets, form a heterocycle with group $A^2$, m is an integer of from 1 to 10, preferably of from 1 to 2, n is an integer of from 1 to 6, preferably 2 or 4, Z is —O—, —C(O)O—, or —C(O)NH—, B is a linear or branched $C_2$-$C_{12}$ polymethylene chain, preferably a $C_3$-$C_6$ one, optionally comprising heteroatoms or heterogroups, such as O or NH, and optionally substituted with one or several hydroxy or amino groups, and $X^-$, which are identical or different, are counter ions.

In a second aspect, the invention relates to a monomer compound comprising several cationic groups having the following formula (I')

$$\text{(I')}$$

wherein:
$R^{1'}$ is H or $CH_3$,
n' is an integer of from 1 to 6, being preferably equal to 3,
Y, which is identical or different is a group of formula —O— or —$NR^{10}$—, wherein $R^{10}$ is hydrogen or an alkyl, hydroxyalkyl, or aminoalkyl $C_1$-$C_6$ linear or branched group,
m', which is identical or different, is an integer of from 1 to 6, being preferably equal to 1,
R, which is identical or different, is a group of formula —$(CH_2)_{p2}$—, wherein p2 is an integer of from 1 to 6, being preferably equal to 3, or a group of formula —$CH_2$—$CH_2$—$N(CH_2$—$CH_2$—$)(CH_2$—$CH_2$—),
s' is an integer of from 1 to 10,
B is a linear or branched $C_2$-$C_{12}$ polymethylene chain, preferably a $C_3$-$C_6$ one, optionally comprising heteroatoms or heterogroups, such as —O— or —NH—, and optionally substituted with one or several hydroxy or amino groups, preferably a group of formula:

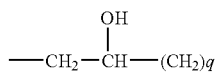

wherein q is an integer of from 1 to 4, being preferably equal to 1.

$R^{2'}$, $R^{3'}$, $R^{4'}$, $R^{5'}$, $R^{6'}$, which are identical or different, are alkyl groups, preferably methyl or ethyl groups, T is terminal organic group different from an ammonium group, a linear or branched hydrocarbon group comprising optionally N, O, or S heteroatoms or heterogroups, optionally substituted, optionally forming or comprising a cycle, for example an alkyl group, or preferably an ammonium group of formula —$N^+R^{7'}R^{8'}R^{9'}$ $X^-$ wherein $R^{7'}$, $R^{8'}$, $R^{9'}$, which are identical or different, are alkyl groups, preferably methyl or ethyl groups, and $X^-$, which are identical or different, are counter ions.

In a third aspect, the invention relates to a monomer compound comprising several cationic groups having the following formula (I")

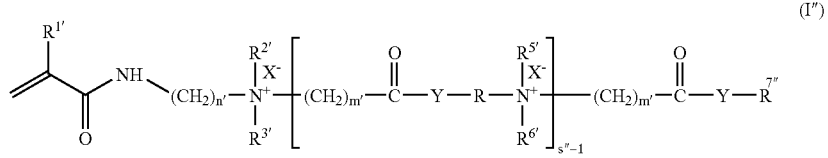

wherein $R^{1'}$ is H or $CH_3$, n' is an integer of from 1 to 6, being preferably equal to 3, Y, which is identical or different, is a group of formula —O— or —$NR^{10}$—, wherein $R^{10}$ is hydrogen or an alkyl, hydroxyalkyl, or aminoalkyl $C_1$-$C_6$ linear or branched group, m', which is identical or different, is an integer of from 1 to 6, being preferably equal to 1, R, which is identical or different, is a group of formula —$(CH_2)_{p2}$—, wherein p2 is an integer of from 1 to 6, being preferably equal to 3, or a group of formula —$CH_2$—$CH_2$—$N(CH_2$—$CH_2$—)($CH_2$—$CH_2$—), s" is an integer of from 2 to 10, preferably equal to 3, $R^{2'}$, $R^{3'}$, $R^{4'}$, $R^{5'}$, $R^{6'}$, which are identical or different, are alkyl groups, preferably methyl or ethyl groups, $X^-$, which are identical or different, are counter ions, and R'" is terminal organic group, different from ammonium, such as a linear or branched hydrocarbon group comprising optionally N, O, or S heteroatoms or heterogroups, optionally substituted, optionally forming or comprising a cycle, for example an alkyl group.

The invention also relates to processes for preparing monomer compounds according to the first aspect and to the second aspect. The invention also relates to polymer comprising repeating polycationic units deriving from said monomer compounds.

DETAILED DESCRIPTION OF THE INVENTION

Monomer Compound

First Aspect

The monomer compound according to the first aspect, is preferably as follows:

Z is —C(O)NH—, n is equal to 2 or 3, being preferably equal to 3, and

B has the following formula:

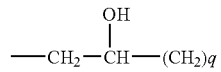

wherein q is an integer of from 1 to 4, being preferably equal to 1.

The monomer compound according to the first aspect wherein m is equal to 1 is an advantageous embodiment.

It is also preferred that:

$A^1$ is —$(CH_2)_{p1}$—, wherein p1 is an integer of from 1 to 6, preferably 1, and $A^2$ is of formula —$(CH_2)_{p2}$— wherein p2 is an integer of from 1 to 6.

In an alternative embodiment, $A^2$ has the following formula —$CH_2$—$CH_2$—$N(CH_2$—$CH_2$—)($CH_2$—$CH_2$—), the group —$N(CH_2$—$CH_2$—)($CH_2$—$CH_2$—) forming a heterocycle comprising two N atoms with the N atom in the brackets and a $R^2$ or $R^3$ group in the brackets.

$R^1$ to $R^6$, which are identical or different, are preferably methyl or ethyl groups, if they do not form a heterocycle with group $A^2$ as mentioned above for the alternative embodiment.

$X^-$, which are identical or different, are preferably halogen, sulfonate, sulfate, hydrogensulfate, phosphate, phosphonate, citrate, formate or acetate anions, such as anions of formula $Cl^-$, $Br^-$, $I^-$, or $CH_3OSO_3^-$.

Second Aspect

The monomer compound according to the second aspect of the invention, has preferably the following formula (II'):

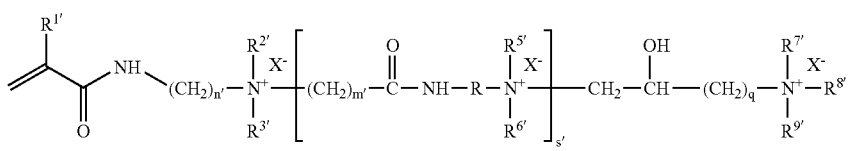
(II')

wherein

R' is H or $CH_3$, n' is an integer of from 1 to 6, being preferably equal to 3, m', which is identical or different, is an integer of from 1 to 6, being preferably equal to 1, q is an integer of from 1 to 4, being preferably equal to 1

R, which is identical or different, is a group of formula —$(CH_2)_{p2}$—, wherein p2 is an integer of from 1 to 6, being preferably equal to 3, s' is an integer of from 1 to 10, being preferably equal to 1, and $R^{2'}$, $R^{3'}$, $R^{4'}$, $R^{5'}$, $R^{5'}$, $R^{7'}$, $R^{8'}$, $R^{9'}$, are methyl groups, and $X^-$ which, are identical or different, are halogen, sulfonate, sulfate, hydrogensulfate, phosphate, phosphonate, citrate, formate or acetate anions, such as anions of formula $Cl^-$, $Br^-$, $I^-$, or $CH_3OSO_3^-$.

In a preferred embodiment of monomer compounds according to the second aspect of the invention, said monomer compound has the following formula:

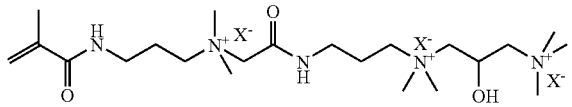

wherein $X^-$, which are identical or different, are anions of formula $Cl^-$, $Br^-$, $I^-$, or $CH_3OSO_3^-$. It is for example N,N,N,N',N',N",N"-heptamethyl-N'''-3-(1-oxo-2-methyl-2-propenyl)aminopropyl-9-oxo-8-azo-decane-1,4,10-triammonium trichloride, having the following formula:

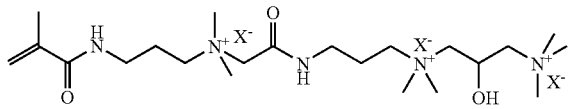

wherein $X^-$ is a chloride anion.

Process

Process First Aspect

The monomer compounds defined above, according to the first aspect of the invention, can be prepared by a process comprising the following steps a) to d):

Step a) optionally, carrying out the following reaction scheme I:

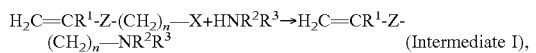 (Intermediate I), wherein Z, $R^1$, $R^2$, $R^3$, X, n are as defined above.

Step a) is optional since intermediate I is usually commercially available.

Step b) carrying out the following reaction schemes II then III

Reaction Scheme II:

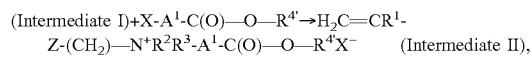 (Intermediate II), wherein X, which is identical or different, and $A^1$ are as defined above, and $R^{4'}$ is an alkyl group, preferably ethyl.

Reaction Scheme III:

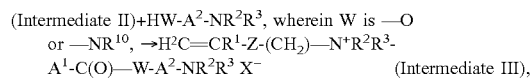 (Intermediate III), wherein $R^2$, $R^3$, which are identical or different, $A^2$ and $R^{10}$, are as defined above.

Step c) implementing (m−1) times the following reaction schemes IIa then IIIa, with identical or different reactants than those used in step b) or in a preceding implementation:

Reaction Scheme IIa:

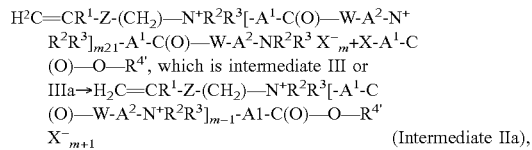 (Intermediate IIa), wherein X and $A^1$, which is identical or different, are as defined above, and $R^{4'}$ is an alkyl group, preferably ethyl, Reaction Scheme IIIa:

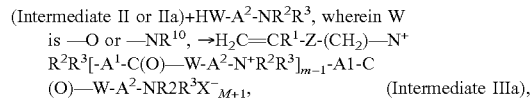 (Intermediate IIIa), wherein $A^2$, $R^{10}$, $R^2$, and $R^3$, which are identical or different, are as defined above.

Step d) carrying out the following reaction scheme IV:

Reaction Scheme IV:

(Intermediate III or IIIa)+X—B—$N^+R^4R^5R^6$ $X^-$→the monomer compound as above, wherein X, B, $R^4$, $R^5$, and $R^6$, which are identical or different, are as defined above.

Process Second Aspect

The monomer compounds defined above, according to the second aspect of the invention, can be prepared by a process comprising the following steps b') to d'):

Step b') carrying out the following reaction schemes II' then III' reaction scheme II':

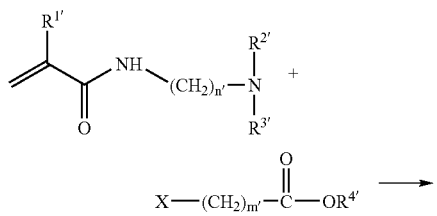

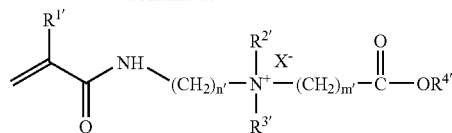

wherein n', m', $R^{1'}$, $R^{2'}$, $R^{3'}$, and X, are as defined above, and $R^{4'}$ is an alkyl group, preferably ethyl.

Typically, a N-Dialkylaminoalkyl (meth)acrylamide monomer is reacted with a chlorocarboxylate, to obtain a cationic ester monomer.

reaction scheme III':

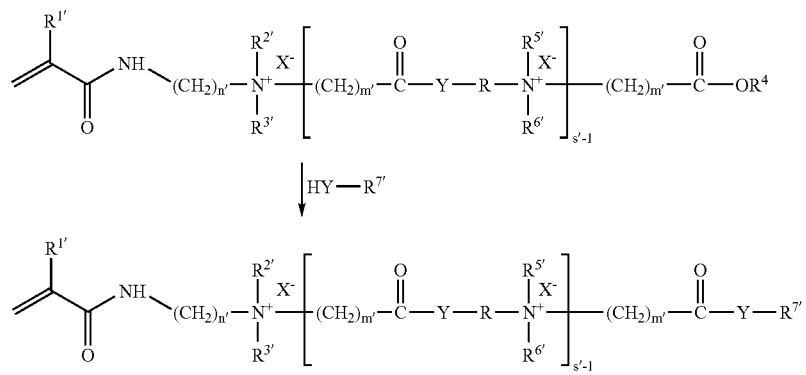

wherein s'=1, $R^{7'}$ is a group of formula $—(CH_2)_{p2}—NR^{5'}R^{6'}$, wherein p2 is an integer of from 1 to 6, being preferably equal to 3, and $R^{5'}$ and $R^{6'}$ are as defined above, or a group of formula $—CH_2—CH_2—N(CH_2—CH_2—)(CH_2—CH_2—)NH$, and Y is $—O—$ or $—NR^{10}$ wherein $R^{10}$ is as defined above.

Typically, the cationic ester monomer undergoes exchange reaction with a functional-bearing organic amine or alcohol to obtain a multifunctionalized cationic monomer. Typically the reaction is carried out with a dialkylaminoalkylamine.

Step c') implementing (s'-1) times the following reaction schemes II'a then III'a, with identical or different reactants than those used in step b') or in a preceding implementation:

reaction scheme II'a:

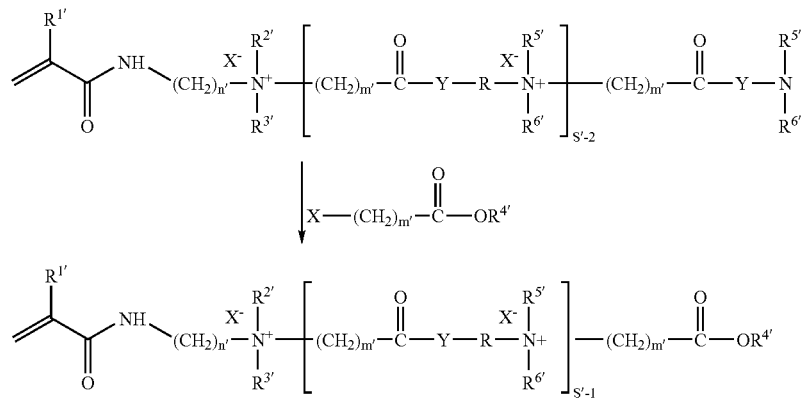

wherein s'>1, n', m', $R^{1'}$, $R^{2'}$, $R^{3'}$, and X, which are identical or different, are as defined above, and $R^{4'}$ is an alkyl group, preferably ethyl.

reaction scheme III'a:

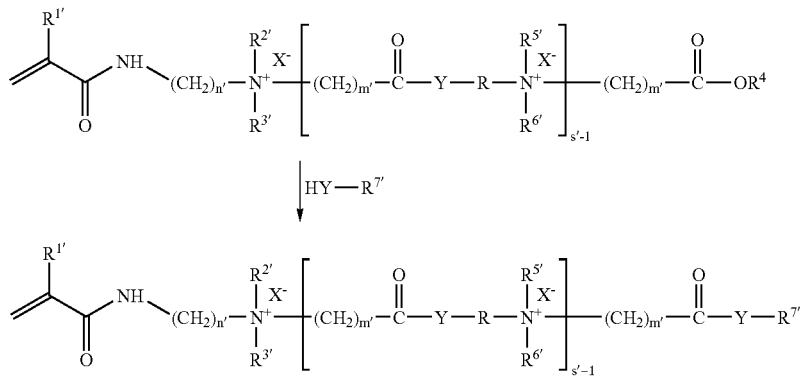

wherein s'>1, $R^{7'}$ is a group of formula $-(CH_2)_{p2}-NR^{5'}R^{6'}$, wherein p2 is an integer of from 1 to 6, being preferably equal to 3, and $R^{5'}$ and $R^{6'}$ are as defined above, or a group of formula $-CH_2-CH_2-N(CH_2-CH_2-)(CH_2-CH_2-)NH$, and Y is $-O-$ or $-NR^{10}$ wherein $R^{10}$ is as defined above.

Step d') carrying out the following reaction scheme IV':

reaction scheme IV':

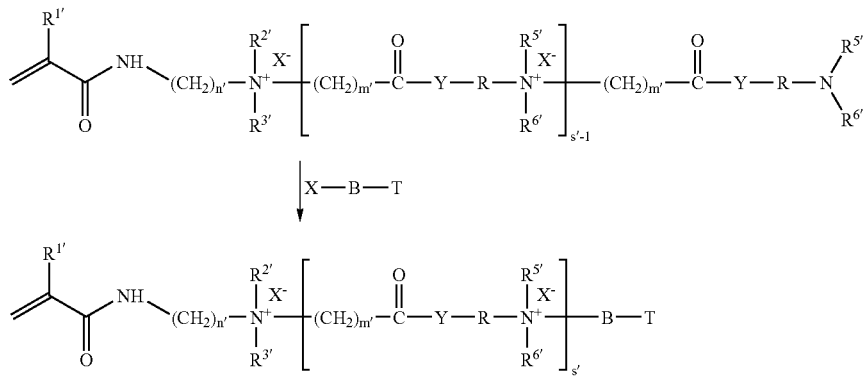

wherein X, B, T, which are identical or different, are as defined above. Typically the reaction is carried out with (3-chloro-2-hydroxpropyl)trimethylammonium chloride (Quat-188).

In a preferred embodiment, the process is the following:

units comprising an anionic group, or potentially anionic group.

Copolymers may be random copolymers, block copolymers, grafted copolymers, or star-shaped copolymers. Random copolymers are preferred.

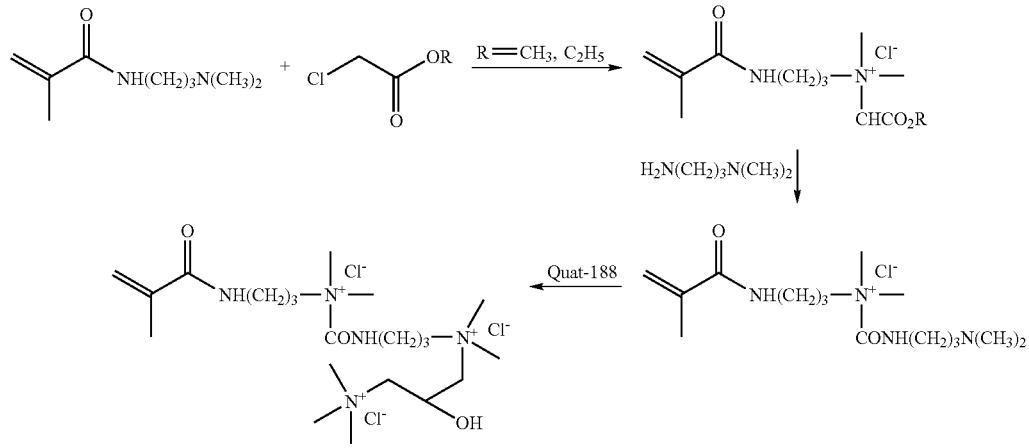

wherein R is $CH_3$ or $C_2H_5$, and QUAT-188 is $Cl-CH_2-CHOH-CH_2-N^+(CH_3)_3\ Cl^-$.

Process Third Aspect

The monomer compounds defined above, according to the third aspect of the invention, can be prepared by a process comprising the following steps b") to d")

Step b"): same step than the step b')

Step c"): implementing (s"−2) times reaction schemes II'a then III'a

Steps d"): implementing reaction scheme III'a with a reactant HY—R$^{7''}$ instead of reactant HY—R$^{7'}$, wherein Y and R$^{7''}$ are groups as defined above. Typically HY—R$^{7''}$ is an alkylaminoalkyl alcohol.

Polymers

The invention also relates to polymers comprising polycationic units, deriving from di-cationic polycationic monomers, preferably from tri-cationic monomers, as defined above. Polymers comprising polycationic units include homopolymers and copolymers, comprising the polycationic units defined above, and other units. The other units include:

cationic units (mono cationic, di-cationic, polycationic different from those defined above), neutral units, or The copolymer advantageously exhibits a molecular mass of at least 1000, advantageously of at least 10,000; it can range up to 20,000,000, advantageously up to 10,000,000.

Except when otherwise indicated, when the term molecular mass is used, it will refer to the weight-average molecular mass, expressed in g/mol. The latter can be determined by aqueous gel permeation chromatography (GPC) or measurement of the intrinsic viscosity in a 1N $NaNO_3$ solution at 30° C.

The copolymers can be obtained according to known techniques for the preparation of copolymers, in particular by polymerization by the radical route of the starting ethylenically unsaturated monomers, which are known compounds or compounds which can be easily obtained by a person skilled in the art by employing conventional synthetic processes of organic chemistry.

Reference may in particular be made to the processes disclosed in U.S. Pat. No. 4,387,017 and EP 156,646.

The radical polymerization is preferably carried out in an environment which is devoid of oxygen, for example in the presence of an inert gas (helium, argon, and the like) or of nitrogen. The reaction is carried out in an inert solvent, preferably ethanol or methanol, and more preferably in water.

The polymerization is initiated by addition of a polymerization initiator. The initiators used are the free radical initiators commonly used in the art. Examples comprise organic peresters (t-butylperoxy pivalate, t-amylperoxy pivalate, t-butylperoxy α-ethylhexanoate, and the like); organic compounds of azo type, for example azobisamidinopropane hydrochloride, azobisisobutyronitrile, azobis(2,4-dimethylvaleronitrile), and the like); inorganic and organic peroxides, for example hydrogen peroxide, benzyl peroxide and butyl peroxide, and the like; redox initiating systems, for example those comprising oxidizing agents, such as persulfates (in particular ammonium or alkali metal persulfates, and the like); chlorates and bromates (including inorganic or organic chlorates and/or bromates); reducing agents, such as sulfites and bisulfites (including inorganic and/or organic sulfites or bisulfites); oxalic acid and ascorbic acid, as well as the mixtures of two or more of these compounds.

The preferred initiators are water-soluble initiators. Sodium persulfate and azobisamidinopropane hydrochloride are in particular preferred.

In an alternative form, the polymerization can be initiated by irradiation using ultraviolet light. The amount of initiators used is generally an amount sufficient can produce initiation of the polymerization. The initiators are preferably present in an amount ranging from 0.001 to approximately 10% by weight with respect to the total weight of the monomers and are preferably in an amount of less than 0.5% by weight with respect to the total weight of the monomers, a preferred amount being situated in the range from 0.005 to 0.5% by weight with respect to the total weight of the monomers. The initiator is added to the polymerization mixture either continuously or noncontinuously.

When it is wished to obtain copolymers of high molecular mass, it is desirable to add fresh initiator during the polymerization reaction. The gradual or noncontinuous addition also makes possible a more efficient polymerization and a shorter reaction time. The polymerization is carried out under reaction conditions which are effective in polymerizing the monomers (a), the monomers (b) and optionally the monomers (c) under an atmosphere devoid of oxygen. The reaction is preferably carried out at a temperature ranging from approximately 30° to approximately 100° and preferably between 60° and 90° C. The atmosphere which is devoid of oxygen is maintained throughout the duration of the reaction, for example by maintaining a nitrogen flow throughout the reaction.

Especially useful copolymers are random copolymer comprising:
polycationic units C deriving from a monomer as defined above,
neutral units N, preferably deriving from ethylenically unsaturated monomers, and
optionally units comprising an anionic group or potentially anionic group, referred to as units B, said units preferably deriving from ethylenically unsaturated monomers.

Potentially anionic groups in a unit are groups that may become anionic in a composition comprising the copolymer, or in an application medium wherein a formulation comprising the copolymer is used. Units comprising an anionic group or potentially anionic group (units B) include
    units that comprise one or several anionic groups,
    units that comprise one or several potentially anionic groups,
    units that comprise amphoteric groups, and
    zwitterionic units.

Such a copolymer has the following formula:

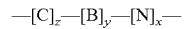

wherein z is greater than 0, y is greater than or equal to 0, x is greater than zero.

Other cationic units include monomers selected from the group of cationic monomers consisting of:
aminoalkyl (meth)acrylates, (meth)aminoalkyl (meth)acrylamides;
monomers comprising at least one secondary, tertiary or quaternary amine function, or a heterocyclic group containing a nitrogen atom, vinylamine or ethylenimine;
diallyldialkyl ammonium salts;
their mixtures, their salts, and macromonomers deriving from therefrom.

Examples of other cationic monomers include:
dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide;
ethylenimine, vinylamine, 2-vinylpyridine, 4-vinylpyridine;
trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and diallyldimethyl ammonium chloride, Preferred other cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, and vinylbenzyl trimethyl ammonium chloride.

Hereinafter, units B, are referred as to units deriving from monomers B. Hereinafter neutral units as referred as to units deriving from monomer N.

Preferred monomers B include:
alpha ethylenically unsaturated monomers comprising a phosphate or phosphonate group,
alpha ethylenically unsaturated monocarboxylic acids,
monoalkylesters of alpha ethylenically unsaturated dicarboxylic acids,
monoalkylamides of alpha ethylenically unsaturated dicarboxylic acids,
alpha ethylenically unsaturated compounds comprising a sulphonic acid group, and salts of alpha ethylenically unsaturated compounds comprising a sulphonic acid group.

Example of monomers B include:
acrylic acid, methacrylic acid,
vinyl sulphonic acid, salts of vinyl sulfonic acid,
vinylbenzene sulphonic acid, salts of vinylbenzene sulphonic acid,
alpha-acrylamidomethylpropanesulphonic acid, salts of alpha-acrylamidomethylpropanesulphonic acid
2-sulphoethyl methacrylate, salts of 2-sulphoethyl methacrylate, acrylamido-2-methylpropanesulphonic acid (AMPS), salts of acrylamido-2-methylpropanesulphonic acid,
styrenesulphonate (SS)
α-ethacrylic acid, β,β-dimethylacrylic acid, methylenemalonic acid, vinylacetic acid, allylacetic acid, ethylidineacetic acid, propylidineacetic acid, crotonic acid, maleic acid, fumaric acid, itaconic acid, citraconic acid, mesaconic acid, N-(methacroyl)alanine, N-(acryloyl)hydroxyglycine, sulfopropyl acrylate, sulfoethyl acrylate, sulfoethyl methacrylate, styrenesulfonic acid, vinylsulfonic acid, vinylphosphonic acid, phosphoethyl acrylate, phophonoethyl acrylate, phosphopropyl acrylate, A preferred copolymer is a copolymer of formula —[C]$_z$—[N]$_x$—, wherein:
C units derive from N,N,N,N',N',N'',N''-heptamethyl-N''-3-(1-oxo-2-methyl-2-propenyl)aminopropyl-9-oxo-8-azodecane-1,4,10-triammonium trichloride,
N units derive from 2-hydroxyethyl acrylate,
x is an integer greater than 1,
z is an integer greater than 1.

Some illustrative but non-limiting examples are provided hereunder for the better understanding of the invention.

A tri-quaternary (meth)acrylate monomer is synthesized as follows:

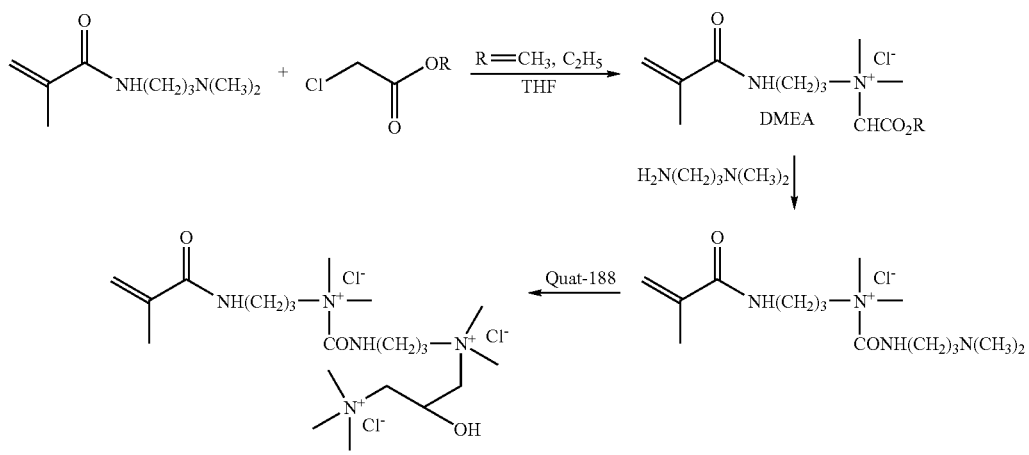

phophonopropyl acrylate, phosphoethyl methacrylate, phophonoethyl methacrylate, phosphopropyl methacrylate, phophonopropyl methacrylate and the alkali metal and ammonium salts thereof.

Preferred monomers N include acrylamide, vinyl alcohol, $C_1$-$C_4$ alkyl esters of acrylic acid and of methacrylic acid, $C_1$-$C_4$ hydroxyalkyl esters of acrylic acid and of methacrylic acid, in particular ethylene glycol and propylene glycol acrylate and methacrylate, polyalkoxylated esters of acrylic acid and of methacrylic acid, in particular the polyethylene glycol and polypropylene glycol esters, esters of acrylic acid or of methacrylic acid and of polyethylene glycol or polypropylene glycol $C_1$-$C_{25}$ monoalkyl ethers, vinyl acetate, vinylpyrrolidone or methyl vinyl ether. Examples of monomers N include:

vinyl acetate, styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, and 2-hydroxyethylacrylate and 2-hydroxyethylmethacrylate.

Some particularly useful copolymers are globally positive, meaning that the number of cationic groups in the copolymer is greater than or the number of anionic groups. According to the copolymer formula above, it means that: z*(number of cationic groups in units C)>y*(number of anionic groups in units B).

DMEA, the ethyl ester quaternized DMAPMA, is obtained from THF with a purity >99% according to HPLC ananlysis. The structure and functional group of DMEA is confirmed by $^1$H and $^{13}$C NMR. Subsequent reaction of DMEA with dimethylaminopropylamine in methanol yields 94% (according to UV absorption at 210 nm) of bifunctional product. A peak corresponding to AP is also detected, which accounts for the impurity (6%). Quaternization of the product from DMEA and DMAPA yields two products with ratio of about 9:1 plus the carried amount of AP monomer. The two quaternized products could be isomers of the Triquat. If this was case, more than 90% of Triquat could be obtained.

A homopolymer is prepared in aqueous solution at 20% solid. Typical property of this batch is shown below:

| | |
|---|---|
| Appearance | Colorless clear liquid |
| Solid | 21.68% |
| Calculated Active Polymer | 21.48% |
| Cationic Charge | 4.84 meq/g |
| pH | 6.27 |
| Residual Monomer | <0.2% |
| B.V. (LV2, 60 rpm, 25° C. | 210 cps |

Alternatively, DMEA is reacted with aminoethylpiperazine and yields a single product plus small amount of AP monomer according to HPLC analysis. This product can be quaternized with Quat-188 into two products that polymerized without gel formation, indicating that the aminolysis is selective and that the two quaternized products are isomers. Without indenting to be bound to any theory, a proposed mechanism is shown below:

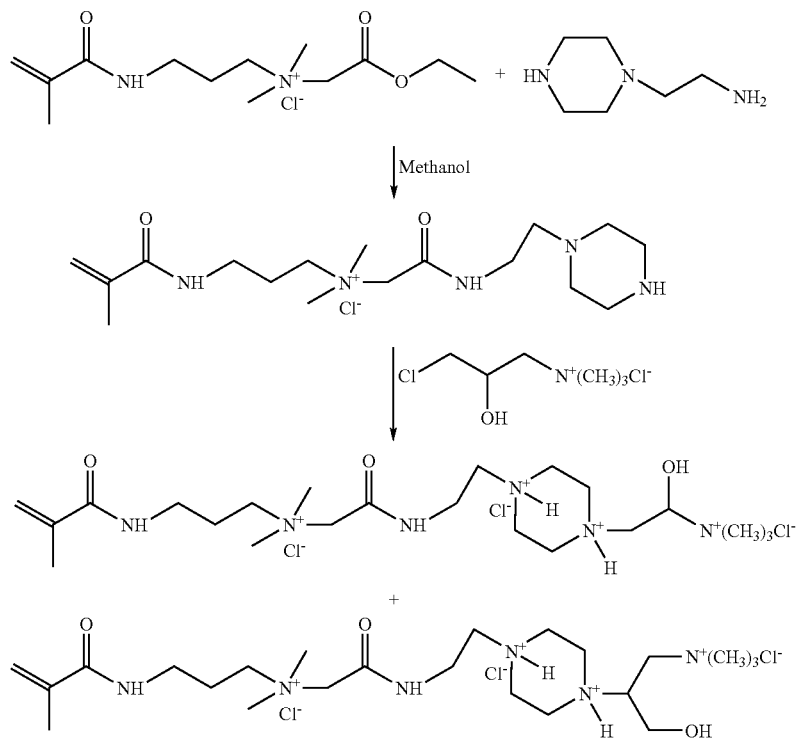

EXAMPLES

Examples #1-3 Demonstrate the Preparation of Monomers

Example #1

This example shows one-pot process to prepare triquat without purification. This was achieved by carrying the three-step reactions in a jacketed reactor flask equipped with mechanic stirrer, gas inlet, condenser and thermometer. The mechanic stirring and air purging were maintained throughout the reactions. Thus, dimethylaminopropyl methacrylamide (DMAPMA), 340.52 g, methyl chloroacetate, 238.75 g, MEHQ, 0.34 g and methanol, 425 g was weighted into the reactor and heated at 65-70° C. for approximately 5 hours to yield (methacrylamidopropyl)(methoxy-carbonylmethyl) dimethylammonium chloride (MMDMAC). Samples were taken every 2 hours and analyzed by HPLC analysis and Cl$^-$ titrated with AgNO$_3$ to ensure 100% conversion (1$^{st}$ step). In the 2$^{nd}$ step, MEHQ, 0.365 g and dimethylaminopropylamine (DMAPA), 224.5 g was slowly was slowly added to MMDMAC solution after it was cooled to room temperature. An exothermic reaction was observed, and the mixture turned into light yellow. Heat was continued at 65-70° C. for 2 hours and then methanol was distilled out under vacuum. After confirmed all ester was converted into amide by HPLC in the 2$^{nd}$ step, then added 65% (3-chloro-2-hydroxypropyl) trimethylammonium chloride (Quat-188), 637 g to proceed to 3$^{rd}$ step. The temperature was kept at 65-70° for 2 hours. During the period, residual amount of methanol was stripped out and water was added to make a solid content of about 55%. The reaction was continued in water for another hour to yield the triquat monomer (3$^{rd}$ step). The product was slightly viscous with a pale yellow color and pH of 7.8. Alternatively, the triquat monomer was prepared by replacing methanol with ethanol, or by replacing methyl chloroacetate with ethyl chloroacetate. The structure of reaction products from each step were confirmed by C-13 NMR measurement. The triquat so synthesized was expected to contain a small amount of multiple quats as impurity due to the slight excess use of choroacetate and DMAPA. The multiple quats were not a concern for polymerization and for the uses of the triquat. If a highly pure triquat or multiple quats is required, the excess amount of chloroacetate and DMAPA can be removed under vacuum before proceeding to next step of reactions. Repeating steps 1 and 2 with or without step 3 would result in higher quats.

Example #2

This example demonstrated how to make pure (methacrylamidopropyl)-(ethoxycarbonylmethyl)dimethylammonium chloride (MEDMAC) or MMDMAC, the intermediate for further functionalization. MEHQ, 0.034 g, DMAPMA, 34.05 g, tetrahydrofuran, 40.0 g and ethyl chloroacetate, 36.9 g was heated at 65-67° C. under reflux and air purging. Phase separation was observed after 10 minutes and the crystallization was observed after about 1 hour of reaction. Tetrahydrofuran 40 g was added, the reaction was continued for another 2 hours, HPLC analysis showed 99.4% of DMAPMA was converted. The solid was filtered out and washed with THF three time and then dried in vacuum overnight to yield MMDMAC, 58.5 g (100% yield with purity >99% by HPLC). MEDMAC was found to react with DMAPM almost quantitatively in methanol at room temperature overnight. Alternatively, pure MMDMAC was prepared from methyl chloroacetate by following the same procedure with equal molar of the chloroacetate.

Example #3

This example demonstrates the preparation of a monomer with morphine heterocycle function in one pot process. DMAPMA, 17.03 g, methyl chloroacetate, 10.85 g, ethanol, 27.8 g was heated at 65° C. under air purging for 5 hours until all DMAPMA was converted. Then aminopropylmorphine, 14.42 g and MEHQ, 0.050 g was added, heating and purging was continued for 3 hours. Methanol was then stripped out and water was added to result in an aqueous solution of the product. Alternatively, equal molar amount of aminoethylpiperazine was used instead of aminopropylmorphine to yield piperazine functionalized monomer. Single peak was observed from HPLC analysis, which indicated that the primary amine was reacted rather the secondary amine on the six-membered ring. Further quaternization with Quat 188 and neautralization resulted in a tetraquat.

Examples #4-5 demonstrate how to prepare homopolymer of Triquat

Example #4

To a reactor equipped with mechanic stirrer, condenser, gas inlet and thermometer was added Triquat monomer at 50% active in water, as prepared in example #1,200 g and deionized water, 300 g. The content was heated to 70° C. under nitrogen purge. Stirring and purging was maintained throughout the reaction. After the temperature reached 70° C. and 1 hour gurging, Wako V-50, 0.05 g was added. The viscosity started to build up after 30 minutes. After 2 hours, another portion of wako V-50, 0.05 g was added, the batch was kept at 70° C. for another hour. Polymerization was continued at 70° C. for another 3 hours, for each hour, sodium persulfate, 0.10 g in 1 ml of deionized water and sodium metabisulfite, 0.20 g in 1 ml of deionized water were added. The product so obtained with Brookfield viscosity of 1070 cps at 25° C., solid of 21.2%, pH of 6.01 and residual triquat less than 500 ppm. The cationic charge density of 4.8 meq/g as titrated with PVSK.

Example #5

The same charge and procedure were followed as of Example #4, except the reaction was done at 75° C., and the $1^{st}$ and $2^{nd}$ shots of initiators were sodium persulfate, 0.10 g in 1 ml deionized water and sodium metabisufite, 0.20 g in 1 ml of deionized water respectively. The product had a solid content of 21.7%, pH of 6.21, viscosity of 210 cps and charge density of 4.84 meq/g.

Example #6

To a reactor equipped with mechanic stirrer, condenser, gas inlet and thermometer was added Triquat monomer at 54.8% active in water, 269.76 g, acrylamide (AM) 50%, 4.35 g, deionized water, 225.9 g. The content was heated to 75° C. under nitrogen purge. The purge and mix were maintained throughout the reaction. After 1 hour purge and the temperature reached 75° C., sodium persulfate, 0.11 g in 2 ml of water was added. The content was hold at 75° C. for 2 hours, and continued for another 2 hours, at the end of each hour, sodium persulfate 0.10 g in 2 ml of water was added to the reaction. The temperature was increased to 85-90° C. after the $3^{rd}$ addition of persulfate and was kept at this temperature for 2 hours. After the content was cooled to 65° C., sodium metabisulfite, 0.2 g in 2 ml of water, was added. The reaction was kept at 65° C. for one hour. Residual monomers of acrylamide and triquat were then checked by HPLC analysis. The last step was repeated until the residual monomer reached an acceptable level. The polymer so obtained was clear, had a viscosity of 1260 cps, solid of 30.2%, pH of 5.48, acrylamide 76 ppm and non-detectable triquat.

Examples #7-14

In these examples, the amount of triquat and acrylamide were varied as shown in Table 1. The reactions were done according to the procedure described in example 6, except the $1^{st}$ shot of initiator and/or the temperature shown in Table 1 were used.

TABLE 1

| # | 54.8% Triquat | 50% AM | Water | $Na_2S_2O_8$ | T (° C.) | comment |
|---|---|---|---|---|---|---|
| 6 | 269.76 | 4.35 | 225.9 | 0.11 | 75 | |
| 7 | 259.04 | 16.1 | 224.87 | 0.15 | 75 | |
| 8 | 241.74 | 35.05 | 223.21 | 0.30 | 75 | |
| 9 | 209.16 | 70.76 | 220.08 | 0.18 | 75 | |
| 10 | 179.01 | 103.81 | 217.18 | 0.22 | 75 | |
| 11 | 156.45 | 128.53 | 215.02 | 0.22 | 75 | |
| 12 | 124.96 | 163.05 | 212.00 | 0.18 | 75 | Extra water added to reduce the viscosity |
| 13 | 77.91 | 214.6 | 207.5 | 0.22 | 75 | gel, not analyzed |
| 14 | 44.44 | 251.3 | 204.5 | 0.22 | 75 | Gel, not analyzed |
| 15 | 124.96 | 163.05 | 212 + 250 | 1.00 | 75 | $2^{nd}$ portion of water added after $1^{st}$ shot of initiator |
| 16 | 54.45 | 150.00 | 372 | 0.13 | 75 | 25 part of NaCl added |
| 17 | 25.10 | 142.00 | 303.8 | 0.13 | 80 | 25.2 part of NaCl added |

The polymer from Examples 14 and 15 were discarded without characterization. The properties of the rest of the products are summarized in Table 2.

TABLE 2

| # | % Solid | Appearance | pH | Viscosity | Triquat (ppm) | AM (ppm) |
|---|---|---|---|---|---|---|
| 6 | 30.15 | Clear | 5.48 | 1260 | Not detectable | 76 |
| 7 | 31.95 | hazy | 5.54 | 1004 | Not detectable | Not detectable |
| 8 | 31.94 | hazy | 5.44 | 1148 | Not detectable | 185 |
| 9 | 27.59 | hazy | 5.18 | 1048 | Not detectable | Not detectable |
| 10 | 27.36 | hazy | 5.12 | 4599 | Not detectable | Not detectable |
| 11 | 30.39 | hazy | 5.05 | 33000 | Not detectable | Not detectable |
| 12 | 21.51 | hazy | 4.96 | 589000 | 1330 | Not detectable |
| 16 | 25.96 | gel | 5.20 | gel | 150 | Not detectable |
| 17 | 25.58 | gel | 4.98 | gel | 72 | Not detectable |

The invention claimed is:

1. A polymer comprising repetitive units deriving from a monomer compound comprising several cationic groups according to formula (1): wherein

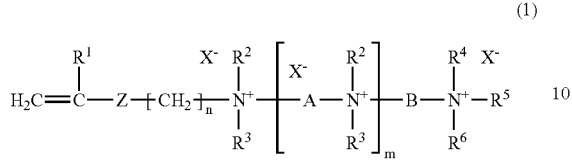

(1)

R$^1$ is a hydrogen atom, a methyl group or an ethyl group,
A, each of which may be identical or different, is a group comprising an ester group of formula -A$^1$-C(O)—O-A$^2$-, or an amide group of formula -A$^1$-C(O)—NR$^{10}$-A$^2$-, wherein:
  R$^{10}$, which is identical or different, is hydrogen or an alkyl, hydroxyalkyl, or aminoalkyl C$_1$-C$_6$ linear or branched group,
  A$^1$, which is identical or different, is a covalent bond or a group of formula —(CH$_2$)$_{p1}$— wherein p1 is an integer of from 1 to 6,
  A$^2$, which is identical or different, is a linear or branched hydrocarbon group comprising optionally N, O, or S heteroatoms or heterogroups, optionally substituted, optionally forming or comprising a cycle,
  R$^1$, R$^2$, R$^3$, R$^4$, R$^5$ and R$^6$, which are identical or different, are hydrogen, alkyl, hydroxyalkyl, or aminoalkyl C$_1$-C$_6$ linear or branched groups, or, if inside the brackets, form a heterocycle with group A2,
m is an integer of from 1 to 10,
n is an integer of from 1 to 6,
Z is —O—, —C(O)O—, or —C(O)NH—,
B is a linear or branched C$_2$-C$_{12}$ polymethylene chain, optionally comprising heteroatoms or heterogroups, and optionally substituted with one or several hydroxy or amino groups, and
X$^-$, each of which may be identical or different, are counter ions.

2. A polymer according to claim 1, being a random, block, star-shape, or grafted copolymer.

3. A polymer according to claim 1, wherein the polymer is a random copolymer comprising:
polycationic-units derived from a monomer according to formula (1), and
neutral units derived from monomers selected from the group consisting of acrylamide, vinyl alcohol, C$_1$-C$_4$ alkyl esters of acrylic acid, C$_1$-C$_4$ alkyl esters of methacrylic acid, C$_1$-C$_4$ hydroxyalkyl esters of acrylic acid, C$_1$-C$_4$ alkyl esters of methacrylic acid, polyalkoxylated esters of acrylic acid, polyalkoxylated esters of methacrylic acid, esters of acrylic acid or of methacrylic acid and of polyethylene glycol or polypropylene glycol, C$_1$-C$_{25}$ monoalkyl ethers, vinyl acetate, vinylpyrrolidone, and methyl vinyl ether.

4. A polymer according to claim 2, wherein m is 1 or 2.

5. A polymer according to claim 3, having the formula:
—[C]$_z$—[N]$_x$—, wherein:
the C units are polycationic units derived from N,N,N,N',N',N'',N''-heptamethyl-N''-3-(1-oxo-2-methyl-2-propenyl)aminopropyl-9-oxo-8-azo-decane-1,4,10-triammonium trichloride,
the N units are neutral units derived from 2-hydroxyethyl acrylate,
x is an integer greater than 1, and
z is an integer greater than 1.

6. A polymer according to claim 3, wherein the neutral units are derived from monomers selected from the group consisting of vinyl acetate, styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate, and 2-hydroxyethylmethacrylate.

7. A polymer according to claim 3, further comprising anionic units derived from monomers selected from the group consisting of alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

8. A polymer according to claim 3, further comprising anionic units derived from monomers selected from the group consisting of acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid, salts of acrylamido-2-methylpropanesulphonic acid, styrenesulphonate, α-ethacrylic acid, β,β-dimethylacrylic acid, methylenemalonic acid, vinylacetic acid, allylacetic acid, ethylidineacetic acid, propylidineacetic acid, crotonic acid, maleic acid, fumaric acid, itaconic acid, citraconic acid, mesaconic acid, N-(methacroyl)alanine, N-(acryloyl)hydroxyglycine, sulfopropyl acrylate, sulfoethyl acrylate, sulfoethyl methacrylate, styrenesulfonic acid, vinylsulfonic acid, vinylphosphonic acid, phosphoethyl acrylate, phophonoethyl acrylate, phosphopropyl acrylate, phophonopropyl acrylate, phosphoethyl methacrylate, phophonoethyl methacrylate, phosphopropyl methacrylate, phophonopropyl methacrylate, and the alkali metal and ammonium salts thereof.

* * * * *